United States Patent
Hong et al.

[11] Patent Number: 6,063,812
[45] Date of Patent: May 16, 2000

[54] FUMAGILLOL DERIVATIVES AND PROCESSES FOR PREPARING THE SAME

[75] Inventors: Chung Il Hong, East Amherst, N.Y.; Jung Woo Kim, Seoul, Rep. of Korea; Sang Joon Lee, Kyunggi-do, Rep. of Korea; Soon Kil Ahn, Seoul, Rep. of Korea; Nam Song Choi, Seoul, Rep. of Korea; Ryung Kee Hong, Seoul, Rep. of Korea; Hyoung Sik Chun, Seoul, Rep. of Korea; Seung Kee Moon, Seoul, Rep. of Korea; Cheol Kyu Han, Seoul, Rep. of Korea

[73] Assignee: Chong Kun Dang Corporation, Rep. of Korea

[21] Appl. No.: 09/311,076

[22] Filed: May 13, 1999

[30] Foreign Application Priority Data

May 15, 1998 [KR] Rep. of Korea .................. 98-17636

[51] Int. Cl.$^7$ ................ A61K 31/335; C07D 303/08; C07D 303/12
[52] U.S. Cl. ................ 514/475; 549/332; 549/539; 549/554; 549/561
[58] Field of Search ................ 514/475; 549/332, 549/539, 554, 561

[56] References Cited

FOREIGN PATENT DOCUMENTS

| 0 354 787 A1 | 2/1990 | European Pat. Off. ............... 303/16 |
| 0 415 294 A2 | 3/1991 | European Pat. Off. ............... 303/22 |

OTHER PUBLICATIONS

Tarbell, D. S., et al., "The Chemistry of Fumagillin," *J. Amer. Chem. Soc.*, 83:3096–3113 (1961).

Marui, S. and Kishimoto, S., "Chemical Modification of Fumagillin. II. 6-Amino-6-deoxyfumagillol and Its Derivatives," *Chem. Pharm. Bull.*, 40:575–579 (1992).

Marui et al., "Chemical Modification of Fumagillin. I. 6-O-Acyl, 6-O-Sulfonyl, 6-O-Alkyl, and 6-O-(N-Substituted-carbamoyl)fumagillols," *Chem. Pharm. Bull.*, 40:96–101 (1992).

Billington, David C., "Angiogenesis and Its Inhibition: Potential New Therapies In Oncology and Non-Neoplastic Diseases," *Drug Design and Discovery*, 8:3–35 (1991).

*Primary Examiner*—Joseph K. McKane
*Assistant Examiner*—Taofiq A. Solola
*Attorney, Agent, or Firm*—Heslin & Rothenberg, P.C.

[57] ABSTRACT

Compounds useful as angiogenesis inhibiting agents and processes for their preparation are disclosed. In one embodiment, the compounds of the invention are represented by Formula 1:

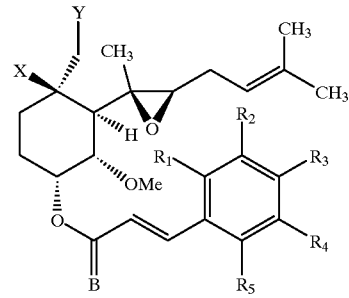

Also disclosed is a pharmaceutical composition for inhibiting angiogenesis in a mammal, said composition comprising a compound of Formula 1, or a pharmaceutically acceptable salt thereof, as an active ingredient.

7 Claims, No Drawings

FUMAGILLOL DERIVATIVES AND PROCESSES FOR PREPARING THE SAME

CLAIM FOR FOREIGN PRIORITY

This application claims the priority of Korean Patent Application No. 1998-17636, filed May 15, 1998.

1. Technical Field

The present invention relates to a novel fumagillol derivative or a pharmaceutically acceptable salt thereof which exhibits excellent angiogenesis inhibiting activities, to a process for preparing the same and to a pharmaceutical composition comprising the same as an active ingredient.

2. Background Art

Angiogenesis is a phenomenon of generating a new capillary vessel, which is one of normal physiological functions as well as one of the pathological functions caused by various diseases. Angiogenesis has a deep connection with growth and transfer of solid cancer, rheumatic arthritis, diabetic retinopathy, psoriasis, or the like [Billington, D. C. Drug Design and Discovery, (1991), 8, 3.]. Judah Folkman of Medical College of Harvard University suggested a novel concept of treating solid cancer by inhibiting angiogenesis in 1971 [J. Folkman, New Engl. Med., (1971), 185, 1182].

Recently, clinical importance of therapeutic agents by means of controlling angiogenesis has been emphasized, and various researches on angiogenesis have been performed. According to clinical results of anticancer medicines using angiogenesis inhibitors, in particular, it is expected that they cause little problems caused by general anticancer medicines, including adverse effect and tolerance. In other word, an angiogenesis inhibitor does not directly act on tumor cells, but acts on endothelial cells of a living organism, and thus, the problem of tolerance does not probably occur, and a synergistic anticancer effect is expected by a therapy in combination with conventional anticancer medicines which have been employed up to the present.

Various fumagillin compounds inhibiting angiogenesis have been reported. For example, it is known that fumagillin having angiogenesis inhibiting action is produced by culturing Aspergillus fumigatus, a productive strain isolated from a soil sample. [Eble, T. E., Hanson, F. R. Antibiotics & chemotherapy, 1, 54 (1951), Eble, T. E., Hanson, F. R. J. Bact., 58, 527 (1949)] [Ingber, G., Fujita, T., Kishimoto, S., Sudo, K., Kanmaru, T., Bre, H., Folkman, J., Nature 248, 555(1990)]

Besides, EP-A-354787, EP-A-357061, JP-A01-233275 and EP-A-415294 have been disclosed; and 6-amino-6-deoxy fumagillol [Chem. Pharm. Bull., (1992), 40, 575], 6-acyl, 6-O-sulfonyl, 6-O-alkyl and 6-O-(N-substituted carbamoyl) fumagillol [Chem. Pharm. Bull., (1992), 40, 10 96] are reported to have angiogenesis inhibiting action.

However, continuous development of angiogenesis inhibitors having less toxicity and more excellent effect is further required.

DISCLOSURE OF THE INVENTION

The present inventors have performed intensive studies to solve the problems described above, and, as a result, developed novel fumagillol derivatives derived from fumagillol, the hydrolyzed product of fumagillin which is produced by fermentation of microorganism, to complete the invention.

The object of the present invention is to provide fumagillol derivatives represented by Chemical Formula 1.

Another object of the present invention is to provide processes for preparing the fumagillol derivatives represented by Chemical Formula 1.

The present invention relates to a fumagillol derivative represented by Chemical Formula 1 or a pharmaceutically acceptable salt thereof:

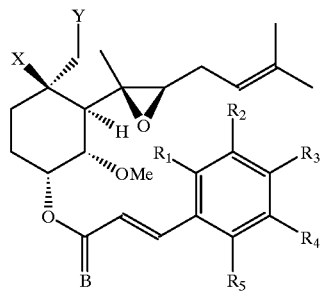

1 herein, X represents hydroxy group and Y represents a halogen, or X and Y may form an oxirane ring;

B represents oxygen or hydrogen; and $R_1$, $R_2$, $R_3$, $R_4$ and $R_5$ independently represent hydrogen, hydroxy, acetoxy, substituted or unsubstituted amino, substituted or unsubstituted alkyl, substituted or unsubstituted aminoalkoxy, $C_1$–$C_6$ alkoxy, halogen, cyano, trifluoromethyl, nitro, alkylenedioxy, formyl, acetamido or methylenoxycarboxyl, provided that $R_1$, $R_2$, $R_3$, $R_4$ and $R_5$ do not represent hydrogen at the same time.

The pharmaceutically acceptable salts of the compound of Chemical Formula 1 include hydrochloride, bromate, sulfate, phosphate, nitrate, formate, acetate, trifluoroacetate, oxalate, fumarate, tartarate, maleate, methanesulfonate, benzensulfonate and p-toluenesulfonate.

Among the compounds of Chemical Formula 1, preferred are those compounds or pharmaceutically acceptable salts thereof, wherein, X represents hydroxy group and Y represents a halogen, or X and Y form an oxirane ring;

B is oxygen or hydrogen; and $R_1$, $R_2$, $R_3$, $R_4$ and $R_5$ independently represent hydrogen, hydroxy, acetoxy, amino, alkylamino, dialkylamino, dialkylaminoalkyl, alkylaminoalkoxy, dialkylaminoalkoxy, $C_1$–$C_6$ alkoxy, halogen, cyano, trifluoromethyl, nitro or methylenedioxy, provided that $R_1$, $R_2$, $R_3$, $R_4$ and $R_5$ do not represent hydrogen at the same time.

Among the compounds of Chemical Formula 1, more preferred are

O-(3,4-dimethoxycinnamoyl)fumagillol;
O-(4-methoxycinnamoyl)fumagillol;
O-(3,4,5-trimethoxycinnamoyl)fumagillol;
O-(4-Chlorocinnamoyl)fumagillol;
4-(3,4,5-trimethoxycinnamoyl)oxy-2-(1,2-epoxy-1,5-dimethyl-4-exenyl)-3-methoxy-1-chloromethyl-1-cyclohexanol;
O-(4-trifluoromethylcinnamoyl)fumagillol;
O-(4-nitrocinnamoyl)fumagillol;
O-(3,4-dimethoxy-6-nitrocinnamoyl)fumagillol;
O-(4-acetoxycinnamoyl)fumagillol;
O-(4-hydroxycinnamoyl)fumagillol;
O-(4-acetoxy-3,5-dimethoxycinnamoyl)fumagillol;
O-3,5-dimethoxy-4-hydroxycinnamoyl)fumagillol;
4-(4-methoxycinnamoyl)oxy-2-(1,2-epoxy-1,5-dimethyl-4-hexenyl)-3-methoxy-1-chloromethyl-1-cyclohexanol;
O-(4-dimethylaminocinnamoyl)fumagillol;
O-(4-aminocinnamoyl)fumagillol;
O-(4-cyanocinnamoyl)fumagillol;

O-(3,4,5-trimethoxycinnamyl)fumagillol;
O-(4-dimethylaminoethoxycinnamoyl)fumagillol;
O-(3-dimethylaminomethyl-4-methoxycinnamoyl) fumagillol;
O-(3,4-methylenedioxycinnamoyl)fumagillol;
O-(3,4-dimethoxy-6-aminocinnamoyl)fumagillol;
O-(4-ethylaminocinnamoyl)fumagillol;
O-(4-ethylaminoethoxycinnamoyl)fumagillol;
O-(4-dimethylaminocinnamoyl)fumagillol; and
4-(4-dimethylaminocinnamoyl)oxy-2-(1,2-epoxy-1,5-dimethyl-4-hexenyl)-3-methoxy-1-chloromethyl-1-cyclohexanol.

The compounds of Chemical Formula 1 may be prepared from the compound represented by Chemical Formula 2 (fumagillol), which is a hydrolyzed product of fumagillin produced by fermentation of microorganisms [Tarbell, D. S. et al., J Am. Chem. Soc., 83, 3096 (1961)].

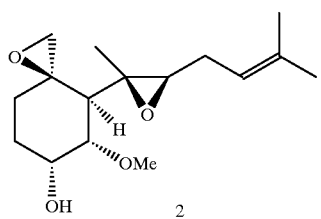

According to a preferred embodiment of the present invention, the compounds represented by Chemical Formula 1 can be prepared via acylation or etherification. The processes are explained by means of Reaction Schemes herein-below:

(1) Acylation

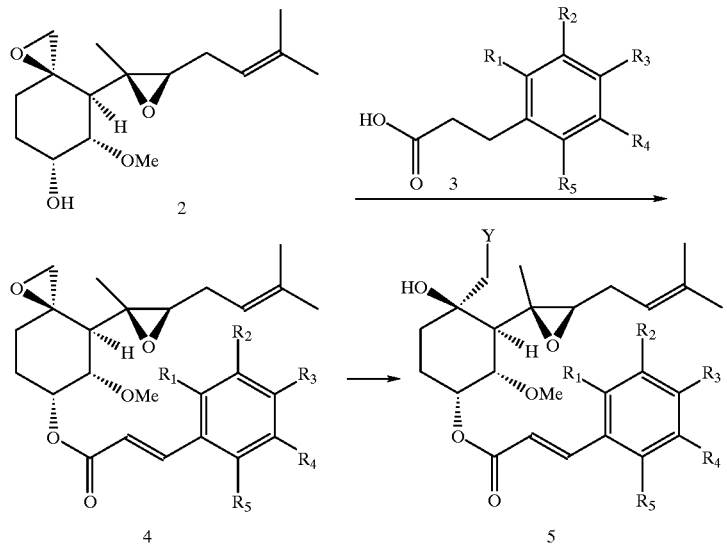

[In the formula, X, Y, $R_1$, $R_2$, $R_3$, $R_4$ and $R_5$ are the same as defined in the above.]

The acylation of Reaction Scheme 1 may be performed by reacting the compound of Chemical Formula 2 as a starting material with a substituted cinnamoyl acid derivative represented by Chemical Formula 3, or a reactive derivative thereof such as an acid anhydride, a mixed anhydride, an acid chloride, an acid p-toluenesulfonic anhydride, an acid mesylic anhydride, a 2-pyridine thiol ester and a phenyl ester, in the presence of a base.

The amount of the compound of Chemical Formula 3 or a reactive derivative thereof used in the acylation may be 1 to 10 equivalents, preferably 1 to 3 equivalents on the basis of the amount of the compound of Chemical Formula 2.

As a base used in the acylation, a tertiary amine such as triethyl amine, diisopropylethyl amine, pyridine and dimethylaminopyridine, or an alkaline metal hydride such as sodium hydride and potassium hydride may be used in an amount of 1 to 10 equivalents. Preferably, triethyl amine, dimethylaminopyridine or sodium hydride may be used in an amount of 1 to 3 equivalents.

As a solvent for the acylation, dimethylformamide, dichloromethane, chloroform, diethyl ether, tetrahydrofuran, dioxane, acetonitrile, benzene or toluene may be used. Among the solvents, preferred are dimethylformamide, dichloromethane, tetrahydrofuran, acetonitrile and benzene.

The reaction temperature of acylation is -80 to 100° C., preferably 0 to 50° C.

The compound of Chemical Formula 4 thus obtained is subjected to oxirane ring opening reaction to provide the compound of Chemical Formula 5.

The oxirane ring opening reaction is performed by reacting the compound of Formula 4 with 1 to 3 equivalents of acid, or reacting with a salt in the presence of an acid catalyst.

As an acid used for the oxirane ring opening reaction, hydrochloric acid, bromic acid or iodic acid may be used, and as a catalyst, acetic acid, sulfuric acid, p-toluenesulfonic acid, hydrochloric acid, phosphoric acid or nitric acid may be used, but preferred is acetic acid or hydrochloric acid.

As a salt for the oxirane ring opening, lithium bromide, lithium chloride, sodium chloride, potassium chloride, potassium bromide, sodium bromide, potassium iodide, sodium iodide or lithium iodide may be used. Among these salts, lithium chloride, lithium bromide and lithium iodide are preferred.

(2) Etherification

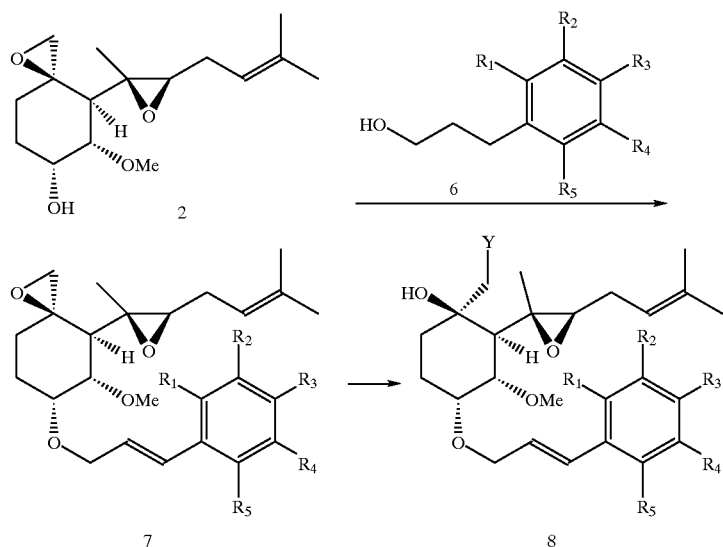

[In the formula, X, Y, $R_1$, $R_2$, $R_3$, $R_4$ and $R_5$ are the same as defined in the above.]

The etherealization of Reaction Scheme 2 is performed by reacting the compound of Chemical Formula 2 as a starting material with a substituted cinnamyl alcohol of Chemical Formula 6 or a reactive derivative thereof such as tosylate, mesylate and halide (chloride, bromide or iodide), in the presence of a base to obtain a compound of Chemical Formula 7.

The amount of the compound of Chemical Formula 6 or a reactive derivative thereof used in the etherification may be 1 to 10 equivalents, preferably 1 to 3 equivalents on the basis of the amount of the compound of Chemical Formula 2. As a base used in the etherification, a tertiary amine such as triethyl amine, diisopropylethyl amine, pyridine and dimethylaminopyridine, or sodium hydride, potassium hydride, butyl lithium, lithium diisopropylamide may be used in an amount of 1 to 10 equivalents, preferably, 1 to 3 equivalents.

As a solvent for the etherification, dimethylformamide, dichloromethane, chloroform, diethyl ether, tetrahydrofuran, dioxane, acetonitrile, benzene or toluene may be used. Among the solvents, preferred are dimethylformamide, dichloromethane, tetrahydrofuran, acetonitrile and benzene.

The reaction temperature of etherealization is −80 to 150° C., preferably 0 to 100° C.

The present invention also provides an angiogenesis inhibiting composition which comprises a therapeutically effective amount of the compound of Chemical Formula 1 or the salt thereof as an active ingredient, and a pharmaceutically acceptable carrier.

A compound of Chemical Formula 1 and a salt thereof according to the present invention may be formulated as a pharmaceutical solid, semisolid or liquid type formulation which is suitable for oral or parenteral administration by blending the compound or salt with a pharmaceutically acceptable inert carrier.

As the compounds of Chemical Formula 1 or salts have excellent angiogenesis inhibiting effect, they can be used as an anticancer medicine or an inhibitor for a cancer transfer, or a therapeutic agent for treating rheumatic arthritis, psoriasis or diabetic retinitis.

In order to evaluate general toxicity of the compound of Chemical Formula 1 according to the present invention, experiments on acute toxicity were carried out by using mice. As a result, the half lethal dose ($LD_{50}$) of each compound in case of oral administration was not less than 2 g/kg, thereby the compound was evaluated as a considerably safe compound.

Thus, the compound of Chemical Formula 1 according to the present invention may be administered in an amount of 0.2 mg/kg to 2 g/kg per day, more preferably 0.2 to 200 mg/kg for the first stage. But the dose may be varied depending on the requirement of a patient, the condition of disease to be treated, and the compound to be used.

The invention is described in more detail by referring to the examples below, but it should be noticed that the present invention is not restricted to the examples by any means.

EXAMPLE 1

O-(3,4-dimethoxycinnamoyl)fumagillol

① To a solution of fumagillol (107 mg) in tetrahydrofuran (5 ml), sodium hydride (46 mg) was added, and the mixture was stirred for an hour.

② To a solution of 3,4-dimethoxycinnamic acid (158 mg) in methylene chloride (5 ml), pyridine (60 mg) was added at room temperature. Oxalyl chloride (96 mg) was added dropwise thereto, and the resultant mixture was stirred for one hour. Then the solvent was removed by evaporation under reduced pressure. To the residue, tetrahydrofuran (3 ml) was added, and the mixture was added dropwise to the solution of ①. After stirring one hour, water (10 ml) was added to the reaction mixture, and the mixture was diluted with ethyl acetate (50 ml). After washing with water (10 ml) and brine (20 ml), the organic layer was dried over anhydrous magnesium sulfate and filtered. The residue was purified by column chromatography (eluent: ethyl acetate/n-hexane =½) to obtain the title compound (84 mg) as a white powder.

$^1$H-NMR (CDCl$_3$) δ: 7.62 (d, 1H, J=15.9 Hz) 7.12~7.05 (m, 2H) 6.86 (d, 1H, J=8.9 Hz) 6.37 (d, 1H, J=15.9 Hz) 5.73 (m, 1H) 5.22 (brt, 1H, J=7.3 Hz) 3.93 (s, 3H) 3.92 (s, 3H)

3.71 (dd, 1H, J=2.8, 11.1 Hz) 3.45 (s, 3H) 3.01 (d, 1H, J=4.3 Hz) 2.58 (t, 1H, J=6.4 Hz) 2.56 (d, 1H, J=4.3 Hz) 2.41~1.81 (m, 6H) 1.75 (s, 3H) 1.66 (s, 3H) 1.24 (s, 3H) 1.18~1.06 (m, 1H)

EXAMPLE 2

O-(4-methoxycinnamoyl)fumagillol

The same procedure as Example 1 was repeated but using fumagillol (500 mg), 60% sodium hydride (120 mg), 4-methoxycinnamic acid (490 mg), pyridine (218 mg) and oxalyl chloride (349 mg), to give 280 mg of the title compound as white solid.

$^1$H NMR (CDCl$_3$) δ: 7.63 (d, 1H, J=15.9 Hz), 7.47 (d, 2H, J=8.7 Hz), 6.90 (d, 2H, J=8.7 Hz), 6.36 (d, 1H, J=15.9 Hz), 5.74 (m, 1H), 5.23 (t, 1H, J=7.4 Hz), 3.84 (s, 3H), 3.71 (dd, 1H, J=11.1, 2.7 Hz), 3.46 (s, 3H), 3.01 (d, 1H, J=4.3 Hz), 2.61 (t, 1H, J=6.4 Hz), 2.57 (d, 1H, J=4.3 Hz), 2.39–1.81 (m, 6H), 1.75 (s, 3H), 1.67 (s, 3H), 1.24 (s, 3H), 1.12 (m, 1H).

EXAMPLE 3

O-(3,4,5-trimethoxycinnamoyl)fumagillol

The same procedure as Example 1 was repeated but using fumagillol (100 mg), 60% sodium hydride (24 mg), 3,4,5-trimethoxycinnamic acid (101 mg), pyridine (43.6 mg) and oxalyl chloride (70 mg), to give 42 mg of the title compound as white solid.

$^1$H NMR (CDCl$_3$) δ: 7.59 (d, 1H, J=15.8 Hz), 6.76 (s, 2H), 6.42 (d, 1H, J=15.8 Hz), 5.73 (m, 1H), 5.22 (t, 1H, J=7.2 Hz), 3.89 (3s, 9H), 3.72 (dd, 1H, J=11.1, 2.6 Hz), 3.46 (s, 3H), 3.01 (d, 1H, J=4.3 Hz), 2.63 (t, 1H, J=6.4 Hz), 2.57 (d, 1H, J=4.3 Hz), 2.37 (m, 1H), 2.19–1.81 (m, 6H), 1.75 (s, 3H), 1.67 (s, 3H), 1.24 (s, 3H), 1.11 (m, 1H).

EXAMPLE 4

O-(chlorocinnamoyl)fumagillol

The same procedure as Example 1 was repeated but using fumagillol (100 mg), 60% sodium hydride (24 mg), 4-chlorocinnamic acid (77 mg), pyridine (43.6 mg) and oxalyl chloride (70 mg), to give 51 mg of the title compound as white solid.

$^1$H NMR (CDCl$_3$) δ: 7.62 (d, 1H, J=16.0 Hz), 7.45 (d, 2H, J=8.5 Hz), 7.36 (d, 2H, J=8.5 Hz), 6.46 (d, 1H, J=16.0 Hz), 5.22 (t, 1H, J=7.7 Hz), 3.71 (dd, J=11.1, 2.8 Hz), 3.46 (s, 3H), 3.01 (d, 1H, J=4.3 Hz), 2.62 (t, 1H, J=6.3 Hz), 2.57 (d, 1H, J=4.3 Hz), 2.38–1.81 (m, 6H), 1.75 (s, 3H), 1.67 (s, 3H), 1.23 (s, 3H), 1.12 (m, 1H)

EXAMPLE 5

4-(3,4,5-trimethoxycinnamoyl)oxy-2-(1,2-epoxy-1,5-dimethyl-4-hexenyl)-3-methoxy-1-chloromethyl-1-cyclohexanol To a solution of compound(100 mg) obtained from Example 3 in tetrahydrofuran, lithium chloride (48 mg) and acetic acid (0.12 ml) were added, and the mixture was stirred at 30° C. for 36 hours. After adding water (10 ml) and ethyl acetate (100 ml) to the reaction mixture, the organic layer was separated, washed with brine (10 ml), dried over anhydrous magnesium sulfate, and filtered. The solvent was evaporated under reduced pressure, and the residue was purified by silica gel column chromatography (eluent: ethyl acetate/n-hexane=½) to obtain the title compound (105 mg) as white solid.

$^1$H NMR (CDCl$_3$) δ: 7.59 (d, 1H, J=15.8 Hz), 6.76 (s, 2H), 6.42 (d, 1H, J=15.8 Hz), 5.73 (m, 1H), 5.22 (t, 1H, J=7.2 Hz), 3.93 (d, 1H, J=11.8 Hz), 3.89 (3s, 9H), 3.72 (dd, 1H, J=11.1, 2.6 Hz), 3.52 (d, 1H, J=11.8 Hz) 3.46 (s, 3H), 3.01 (d, 1H, J=4.3 Hz), 2.63 (t, 1H, J=6.4 Hz), 2.57 (d, 1H, J=4.3 Hz), 2.37–1.81 (m, 6H), 1.75 (s, 3H), 1.67 (s, 3H), 1.24 (s, 3H), 1.11 (m, 1H).

EXAMPLE 6

O-(4-trifluoromethylcinnamoyl)fumagillol

The same procedure as Example 1 was repeated but using fumagillol (100 mg), 60% sodium hydride (24 mg), 4-trifluoromethylcinnamic acid (101 mg), pyridine (43.6 mg) and oxalyl chloride (70 mg), to give 31 mg of the title compound as white solid.

$^1$H-NMR (CDCl$_3$) δ: 7.68 (d, 1H, J=14.4 Hz), 7.62~7.61 (m, 4H), 6.56 (d, 1H, J=14.4 Hz), 5.77(m, 1H), 5.21 (brt, 1H), 3.72 (dd, 1H, J=2.8, 11.1 Hz), 3.46 (s, 3H), 3.01 (d, 1H, J=4.3 Hz), 2.63 (t, 1H, J=6.3Hz), 2.57(d, 1H, J=4.3 Hz), 2.39~1.85(m, 6H), 1.75(s, 3H), 1.66(s, 3H), 1.23(s, 3H), 1.16~1.07(m, 11H)

EXAMPLE 7

O-(4-nitrocinnamoyl)fumagillol

The same procedure as Example 1 was repeated but using fumagillol (100 mg), 60% sodium hydride (24 mg), 4-nitrocinnamic acid (101 mg), pyridine (43.6 mg) and oxalyl chloride (70 mg), to give 66 mg of the title compound as white solid.

$^1$H-NMR (CDCl$_3$) δ: 8.25 (d, 2H, J=8.8Hz), 7.71~7.66 (m, 3H), 6.61 (d, 1H, J=16.1 Hz), 5.78 (m, 1H), 5.22 (t, 1H, J=6.9 Hz), 3.72 (dd, 1H, J=2.8, 11.2 Hz), 3.46 (s, 3H), 3.02 (d, 1H, J=4.4 Hz), 2.61 (t, 1H, J=6.4Hz), 2.58 (d, 1H, J=4.4 Hz), 2.43~1.85 (m, 6H), 1.75 (s, 3H), 1.66 (s, 3H), 1.23 (s, 3H), 1.17~1.08 (m, 1H)

EXAMPLE 8

O-(3,4-dimethoxy-6-nitrocinnamoyl)fumagillol

The same procedure as Example 1 was repeated but using fumagillol (100 mg), 60% sodium hydride (24 mg), 3,4-dimethoxy-5-nitrocinnamic acid (179 mg), pyridine (43.6 mg) and oxalyl chloride (70 mg), to give 42 mg of the title compound as white solid.

$^1$H-NMR (CDCl$_3$) δ: 8.23 (d, 1H, J=15.7 Hz), 7.65 (s, 1H), 7.04(s, 1H), 6.35 (d, 1H, J=15.7 Hz), 5.78 (m, 1H), 5.20 (brt, 1H, J=7.2 Hz), 4.05 (s, 3H), 3.98 (s, 3H), 3.73 (dd, 1H, J=2.8, 11.1 Hz), 3.47 (s, 3H), 3.01 (d, 1H, J=4.4 Hz), 2.61 (t, 1H, J=6.4 Hz), 2.57 (d, 1H, J=4.4Hz), 2.39~1.85 (m, 6H), 1.74 (s, 3H), 1.65 (s, 3H), 1.23 (s, 3H), 1.18~1.05 (m, 1H)

EXAMPLE 9

O-(4-acetoxycinnamoyl)fumagillol

The same procedure as Example 1 was repeated but using fumagillol (72 mg), 60% sodium hydride (17 mg), 4-acetoxycinnamic acid (105 mg), pyridine (31 mg) and oxalyl chloride (49 mg), to give 31 mg of the title compound as white solid.

$^1$H-NMR (CDCl$_3$) δ: 7.49 (d, 1H, J=15.9 Hz), 7.28~7.26 (m, 2H), 6.82 (d, 2H, J=8.6 Hz), 6.1 (d, 1H, J=15.9 Hz), 5.75 (m, 1H), 5.22 (t, 1H, J=5.7 Hz), 3.73(dd, 1H, J=2.8, 11.1 Hz), 3.44 (s, 3H), 3.01 (d, 1H, J=4.3 Hz), 2.68 (t, 1H, J=6.3

Hz), 2.57(d, 1H, J=4.3 Hz), 2.48~1.82(m, 6H), 2.38 (s, 3H), 1.76(s, 3H), 1.67(s, 3H), 1.26(s, 3H), 1.18~1.05(m, 1H)

EXAMPLE 10

O-(4-hydroxycinnamoyl)fumagillol

To a solution of the compound (50 mg) obtained from Example 9 in mixed solvent of water:methanol=1:1 (1 ml), sodium hydrogen carbonate (15 mg) was added, and the mixture was stirred for 12 hours.

The reaction mixture was diluted with ethyl acetate (30 ml), and the organic layer was washed with water (10 ml) and brine (20 ml). After drying the organic layer over anhydrous magnesium sulfate and filtering, the residue was purified by column chromatography (eluent: ethyl acetate/n-hexane=1/1) to obtain 36 mg of the title compound as white powder.

$^1$H-NMR (CDCl$_3$) δ: 7.49 (d, 1H, J=15.9 Hz), 7.28~7.26 (m, 2H), 6.82 (d, 2H, J=8.6 Hz), 6.1 (d, 1H, J=15.9 Hz), 5.75 (m, 1H), 5.22 (t, 1H, J=5.7 Hz), 3.73(dd, 1H, J=2.8, 11.1 Hz), 3.44 (s, 3H), 3.01 (d, 1H, J=4.3 Hz), 2.68 (t, 1H, J=6.3 Hz), 2.57(d, 1H, J=4.3 Hz), 2.48~1.82(m, 6H), 1.76(s, 3H), 1.67(s, 3H), 1.26(s, 3H), 1.18~1.05(m, 1H)

EXAMPLE 11

O-(4-acetoxy-3,5-dimethoxycinnamoyl)fumagillol

The same procedure as Example 1 was repeated but using fumagillol (100 mg), 60% sodium hydride (24 mg), 4-acetoxy-3,5-dimethoxycinnamic acid(188 mg), pyridine (43.6 mg) and oxalyl chloride (70 mg), to give 56 mg of the title compound as white solid.

$^1$H-NMR (CDCl$_3$) δ: 7.60 (d, 1H, J=15.9 Hz), 6.78 (s, 2H), 6.44 (d, 1H, J=15.9 Hz), 5.72(m, 1H), 5.22 (brt, 1H), 3.86 (s, 6H), 3.72 (dd, 1H, J=2.8, 11.1 Hz), 3.45 (s, 3H), 3.01 (d, 1H, J=4.3 Hz), 2.63 (t, 1H,J=6.3 Hz), 2.57 (d, 1H, J=4.3 Hz), 2.34 (s, 3H), 2.39~1.85 (m, 6H), 1.75 (s, 3H), 1.66 (s, 3H), 1.23 (s, 3H), 1.16~1.07 (m, 1H)

EXAMPLE 12

O-(3,5-dimethoxy-4-hydroxycinnamoyl)fumagillol

The same procedure as Example 10 was repeated but using the compound of Example 11(40 mg), to give 26 mg of the title compound as white solid.

$^1$H-NMR (CDCl$_3$) δ: 7.58 (d, 1H, J=15.9 Hz), 6.78 (s, 2H), 6.37 (d, 1H, J=15.9 Hz), 5.75 (s, 1H), 5.72 (m, 1H), 5.22 (brt, 1H), 3.93 (s, 6H), 3.71 (dd, 1H, J=2.8, 11.1 Hz), 3.45 (s, 3H), 3.01 (d, 1H, J=4.4 Hz), 2.63 (t, 1H,J=6.4 Hz), 2.57(d, 1H, J=4.4 Hz), 2.45~1.82(m, 6H), 1.75(s, 3H), 1.66(s, 3H), 1.09(s, 3H), 1.18~1.05(m, 1H)

EXAMPLE 13

4-(4-methoxycinnamoyl)oxy-2-(1,2-epoxy-1,5-dimethyl-4-hexenyl)-3-methoxy-1-chloromethyl-1-cyclohexanol The same procedure as Example 5 was repeated but using the compound of Example 2(150 mg), lithium chloride (21 mg) and acetic acid (60 µl), to give 120 mg of the title compound as white solid.

$^1$H-NMR (CDCl$_3$) δ: 7.67 (d, 1H, J=15.9 Hz), 7.49 (d, 2H, J=8.8 Hz), 6.91 (d, 2H, J=8.8 Hz), 5.59 (m, 1 H), 5.19 (brt, 1H, J=6.6 Hz), 3.90 (d, 1H, J=10.9 Hz), 3.84 (s, 3H), 3.50 (d, 1H, J=10.9 Hz), 3.32 (s, 3H), 2.99(t, 1H, J=6.6 Hz), 2.65~1.32 (m, 7H), 1.73 (s, 3H), 1.66 (s, 3H), 1.23 (s, 3H)

EXAMPLE 14

O-(4-dimethylaminocinnamoyl)fumagillol

1) To a solution of 4-dimethylaminocinnamic acid (950 mg) in toluene (20 ml), dipyridyl disulfide (1.64 g) and triphenyl phosphine (1.97 g) were added, and the mixture was stirred for 12 hours.

2) The resultant solution of 1) was added to fumagillol (500 mg) at room temperature. Sodium hydride (142 mg) was added thereto, and the reaction mixture was stirred for 30 minutes. After adding saturated ammonium chloride solution (20 ml), the reaction mixture was extracted with ethyl acetate (100 ml). The organic layer was washed with brine and dried over anhydrous magnesium sulfate. After filtering, the solvent was distilled off under reduced pressure, and the residue was purified by column chromatography (eluent: ethyl acetate/n-hexane=1/2) to obtain yellow solid (470 mg).

$^1$H-NMR (CDCl$_3$) δ: 7.60 (d, 1H, J=15.8 Hz), 7.41 (d, 2H, J=8.9 Hz), 6.67 (d, 2H, J=8.9 Hz), 6.27 (d, 1H, J=15.8 Hz), 5.71 (m, 1H), 5.22 (brt, 11H), 3.70 (dd, 1H, J=2.8, 11.0 Hz), 3.45 (s, 3H), 3.02 (s, 6H), 3.01 (d, 1H, J=4.3 Hz), 2.63 (t, 1H, J=6.3 Hz), 2.56 (d, 1H, J=4.3 Hz), 2.41~1.81 (m, 6H), 1.75 (s, 3H), 1.67 (s, 3H), 1.22 (s, 3H), 1.15~1.06 (m, 1H)

EXAMPLE 15

O-(4-aminocinnamoyl)fumagillol

To a solution of nickel acetate (62 mg) in methanol (2 ml), boron exchange resin (680 mg) was added, and the mixture was stirred for 20 minutes. A solution of the compound (250 mg) obtained in Example 7 in methanol (5 ml) was added thereto at room temperature, and the resultant mixture was stirred for 30 minutes. The boron exchange resin was filtered off, and the solvent was distilled off under reduced pressure. The residue was purified by column chromatography (eluent: ethyl acetate/n-hexane=1/2) to obtain yellow oil (100 mg).

$^1$H-NMR (CDCl$_3$) δ: 7.57 (d, 1H, J=15.9 Hz), 7.33 (d, 2H, J=8.4Hz), 6.54 (d, 2H, J=8.4 Hz), 6.27 (d, 1H, J=15.9 Hz), 5.72 (m, 1H), 5.22 (brt, 1H, J=7.9 Hz), 3.70 (dd, 1H, J=2.7, 11.1 Hz), 3.45 (s, 3H), 3.01 (d, 1H, J=4.3Hz), 2.62 (t, 1H, 6.5 Hz), 2.56 (d, 1H, J=4.3 Hz), 2.37~1.81 (m, 6H), 1.75 (s, 3H), 1.66 (s, 3H), 1.23 (s, 3H), 1.16~1.05 (m, 1H)

EXAMPLE 16

O-(4-cyanocinnamoyl)fumagillol

1) To a solution of 4-cyanocinnamic acid (17 mg) in tetrahydrofuran (2 ml), dicyclohexyl carbodiimide (37 mg), phenol (10 mg) and 4-dimethylaminopyridine (2 mg) were added, and the mixture was stirred at room temperature for 18 hours.

2) To a solution of fumagillol (5 mg) in tetrahydrofuran (1 ml), sodium hydride (2 mg) was added, and the mixture was stirred at room temperature for 30 minutes. The solution obtained from 1) was added dropwise thereto, and the resultant mixture was stirred for 30 minutes. After adding water (2 ml), the reaction mixture was extracted with ethyl acetate (3×30 ml). The combined organic layer was washed with brine, dried over anhydrous magnesium sulfate, filtered, and evaporated under reduced pressure to remove the solvent. The residue was purified by column chromatography (eluent:ethyl acetate/n-hexane=1/2) to obtain 4 mg of white solid.

¹H-NMR (CDCl₃) δ: 7.69~7.54 (m, 5H), 6.57 (d, 1H, J=16.1 Hz), 5.77 (m, 1H), 5.22 (brt, 1H, J=6.9 Hz), 3.71 (dd, 1H, J=2.8, 11.1 Hz), 3.46 (s, 3H), 3.01 (d, 1H, J=4.3 Hz), 2.61 (t, 1H, J=6.4 Hz), 2.19 (d, 1H, J=4.3 Hz), 2.42~1.81 (m, 6H), 1.74 (s, 3H), 1.66 (s, 3H), 1.23 (s, 3H), 1.16~1.04 (m, 11H)

EXAMPLE 17

O-(3,4,5-trimethoxycinnamyl)fumagillol

To a solution of fumagillol (600 mg) in tetrahydrofuran (10 ml), sodium hydride (130 mg) was added, and the mixture was stirred at room temperature for 1 hour. A solution of trimethoxycinnamyl bromide (600 mg) in dimethylformamide (10 ml) was added thereto, and the resultant mixture was stirred at room temperature for 1 hour. After removing the solvent by evaporation under reduced pressure, the residue was purified by column chromatography (eluent: ethyl acetate/n-hexane=1/2) to obtain 550 mg of white solid.

¹H-NMR (CDCl₃) δ: 6.62 (s, 2H), 6.53~6.49 (m, 1H), 6.29~6.23 (m, 1H), 5.20 (brt, 1H, J=7 Hz), 4.28 (d, 1H, J=6 Hz), 4.13(m, 1H), 3.87 (s, 6H), 3.84 (s, 3H), 3.58 (dd, 1H, J=2.4, 11.1 Hz), 3.46 (s, 3H), 2.95 (d, 1H, J=4.3 Hz), 2.57 (t, 1H, 6.5 Hz), 2.51 (d, 1H, J=4.3 Hz), 2.41~1.92 (m, 6H), 1.74 (s, 3H), 1.65 (s, 3H), 1.21 (s, 3H), 1.06~0.98 (m, 1H)

EXAMPLE 18

O-(4-dimethylaminoethoxycinnamoyl)fumagillol

① To a solution of fumagillol (190 mg) in tetrahydrofuran (10 ml), sodium hydride (80 mg) was added, and the mixture was stirred for 1 hour.

② To a solution of 4-dimethylaminoethoxycinnamic acid (240 mg) in benzene (20 ml), thionyl chloride (240 mg) was added at room temperature, and the mixture was heated under reflux for 1 hour. The solvent was removed by evaporation under reduced pressure, and tetrahydrofuran (10 ml) was added to the residue. The solution was added dropwise to the solution obtained from ①, and the mixture was stirred for 1 hour. After adding water (20 ml), the reaction mixture was diluted with ethyl acetate (100 ml). The organic layer was washed with water (20 ml) and brine (40 ml), dried over anhydrous magnesium sulfate, and filtered. The residue was purified by column chromatography (eluent: methanol/chloroform=1/6) to obtain the title compound (60 mg) as white powder.

¹H-NMR (CDCl₃) δ: 7.62 (d, 1H, J=15.9 Hz), 7.46 (d, 2H, J=8.7 Hz) 6.91 (d, 2H, J=8.7Hz) 6.36 (d, 1H, J=15.9Hz) 5.73 (m, 1H) 5.22 (brt, 1H, J=7.3Hz) 4.12 (t, 2H, J=5.6 Hz) 3.71 (dd, 1H, J=2.8, 11.1 Hz) 3.45 (s, 3H) 3.01 (d, 1H, J=4.3 Hz) 2.79 (t, 2H, J=5.6 Hz) 2.58 (t, 1H, J=6.4 Hz) 2.56 (d, 1H, J=4.3 Hz) 2.37 (s, 6H) 2.20~1.81 (m, 6H) 1.75 (s, 3H) 1.66 (s, 3H) 1.24 (s, 3H) 1.18~1.06 (m, 1H)

EXAMPLE 19

O-(3-dimethylaminomethyl-4-methoxycinnamoyl) fumagillol

① To a solution of fumagillol (20 mg) in tetrahydrofuran (2 ml), sodium hydride (9 mg) was added, and the mixture was stirred for 1 hour.

② To a solution of 3-dimethylaminomethyl-4-methoxycinnamic acid (25 mg) in benzene (2 ml), thionyl chloride (25 mg) was added at room temperature, and the mixture was heated under reflux for 1 hour. The solvent was removed by evaporation under reduced pressure, and tetrahydrofuran (1 ml) was added to the residue. The solution was added dropwise to the solution obtained from ①, and the mixture was stirred for 1 hour. After adding water (2 ml), the reaction mixture was diluted with ethyl acetate (10 ml). The organic layer was washed with water (2 ml) and brine (4 ml), dried over anhydrous magnesium sulfate, and filtered. The residue was purified by column chromatography (eluent: methanol/chloroform=1/5) to obtain the title compound (5 mg) as white powder.

¹H-NMR (CDCl₃) δ: 7.62 (d, 1H, J=15.9 Hz) 7.10 (m, 2H) 6.94 (d, 1H, J=8.9 Hz) 6.37 (d, 1H, J=15.9 Hz) 5.73 (m, 1H) 5.22 (brt, 1H, J=7.3 Hz) 3.93 (s, 3H) 3.82 (s, 2H) 3.71 (dd, 1H, J=2.8, 11.1 Hz) 3.45 (s, 3H) 3.01 (d, 1H, J=4.3 Hz) 2.58 (t, 1H, J=6.4 Hz) 2.56 (d, 1H, J=4.3 Hz) 2.37 (s, 6H) 2.20~1.81 (m, 6H) 1.75 (s, 3H) 1.66 (s, 3H) 1.24 (s, 3H) 1.18~1.06 (m, 1H)

EXAMPLE 20

O-(3,4-methylenedioxycinnamoyl)fumagillol

The same procedure as Example 1 was repeated but using fumagillol (500 mg), 60% sodium hydride (120 mg), 3,4-methylenedioxycinnamic acid (490 mg), pyridine (218 mg) and oxalyl chloride (349 mg), to give 280 mg of the title compound as white solid.

¹H-NMR (CDCl₃) δ: 7.62 (d, 1H, J=15.9 Hz) 7.21~7.08 (m, 2H) 6.86 (s, 1H) 6.37 (d, 1H, J=15.9 Hz) 5.73 (m, 1H) 5.31(s, 2H) 5.22 (brt, 1H, J=7.3 Hz) 3.71 (dd, 1H, J=2.8, 11.1 Hz) 3.45 (s, 3H) 3.01 (d, 1H, J=4.3 Hz) 2.58 (t, 1H, J=6.4 Hz) 2.56 (d, 1H, J=4.3 Hz) 2.41~1.81 (m, 6H) 1.75 (s, 3H) 1.66 (s, 3H) 1.24 (s, 3H) 1.18~1.06 (m, 1H)

EXAMPLE 21

O-(3,4-dimethoxy-6-aminocinnamoyl)fumagillol

The same procedure as Example 15 was repeated but using the compound (200 mg) of Example 8, boron exchange resin (420 mg) and nickel acetate (41 mg), to give 105 mg of the title compound as white solid.

¹H-NMR (CDCl₃) δ: 7.57 (d, 1H, J=15.7 Hz) 7.31 (s, 1H) 7.04(s, 1H) 6.35 (d, 1H, J=15.7 Hz) 5.78 (m, 1H) 5.20 (brt, 1H, J=7.2 Hz) 4.05 (s, 3H) 3.93 (s, 3H) 3.92 (s, 3H) 3.73 (dd, 1H, J=2.8, 11.1 Hz) 3.47 (s, 3H) 3.01 (d, 1H, J=4.4 Hz) 2.61 (t, 1H, J=6.4 Hz) 2.57 (d, 1H, J=4.4 Hz) 2.39~1.85 (m, 6H) 1.74 (s, 3H) 1.65 (s, 3H) 1.23 (s, 3H) 1.18~1.05 (m, 1H)

EXAMPLE 22

O-(4-ethylaminocinnamoyl)fumagillol

To a solution of the compound obtained from Example 15 (60 mg) and acetaldehyde (20 mg) in methanol (2 ml), acetic acid (8 mg) was added at room temperature, and then sodium cyanoborohydride (9 mg) was added thereto. After stirring for 1 hour, the reaction mixture was diluted with ethyl acetate (50 ml), and the organic layer was washed with saturated sodium hydrogen carbonate solution (10 ml), water (10 ml) and brine (20 ml), dried over anhydrous magnesium sulfate, and filtered. The residue was purified by column chromatography (eluent:ethyl acetate/n-hexane=1/2) to obtain the title compound (19 mg) as yellow oil.

¹H-NMR (CDCl₃) δ: 7.60 (d, 1H, J=15.8Hz) 7.41 (d, 2H, J=8.9 Hz) 6.67 (d, 2H, J=8.9 Hz) 6.27 (d, 1H, J=15.8 Hz) 5.71 (m, 1H) 5.22 (brt, 1H) 3.70 (dd, 1H, J=2.8, 11.0 Hz)

3.45 (s, 3H) 3.09 (q, 2H, J=6.5Hz) 3.01 (d, 1H, J=4.3 Hz) 2.63 (t, 1H, J=6.3 Hz) 2.56 (d, 1H, J=4.3 Hz) 2.41~1.81 (m, 6H) 1.75 (s, 3H) 1.67 (s, 3H) 1.22 (s, 3H) 1.18(t, 3H, J=6.5 Hz) 1.15~1.06 (m, 1H)

EXAMPLE 23

O-(4-ethylaminoethoxycinnamoyl)fumagillol

The same procedure as Example 18 was repeated but using fumagillol (190 mg), sodium hydride (80 mg) and 4-ethylaminoethoxycinnamic acid (240 mg), to give 73 mg of the title compound as white solid.

$^1$H-NMR (CDCl$_3$) δ: 7.62 (d, 1H, J=15.9 Hz) 7.46 (d, 2H, J=8.7 Hz) 6.91 (d, 2H, J=8.7 Hz) 6.36 (d, 1H, J=15.9 Hz) 5.73 (m, 1H) 5.22 (brt, 1H, J=7.3 Hz) 4.12 (t, 2H, J=5.6 Hz) 3.71 (dd, 1H, J=2.8, 11.1 Hz) 3.45 (s, 3H) 3.01 (d, 1H, J=4.3 Hz) 2.79 (t, 2H, J=5.6 Hz) 2.63 (q, 2H, J=6.8 Hz) 2.58 (t, 1H, J=6.4 Hz) 2.56 (d, 1H, J=4.3 Hz) 2.20~1.81 (m, 6H) 1.75 (s, 3H) 1.66 (s, 3H) 1.24 (s, 3H) 1.22(t, 3H, J=6.8 Hz) 1.18~1.06 (m, 1H)

EXAMPLE 24

O-(4-dimethylaminocinnamyl)fumagillol

The same procedure as Example 17 was repeated but using fumagillol (600 mg), sodium hydride (130 mg) and dimethylaminocinnamyl bromide (570 mg), to give 250 mg of the title compound as white solid.

$^1$H-NMR (CDCl$_3$) δ: 6.62 (s, 2H) 6.53~6.49 (m, 1H) 6.29~6.23 (m, 1H) 5.20 (brt, 1H, J=7 Hz) 4.28 (d, 1H, J=6 Hz) 4.13(m, 1H) 3.70 (dd, 1H, J=2.8, 1.0 Hz) 3.45 (s, 3H) 3.02 (s, 6H) 3.01 (d, 1H, J=4.3 Hz) 2.63 (t, 1H, J=6.3 Hz) 2.56 (d, 1H, J=4.3 Hz) 2.41~1.81 (m, 6H) 1.75 (s, 3H) 1.67 (s, 3H) 1.22 (s, 3H) 1.15~1.06 (m, 1H)

EXAMPLE 25

4-(4-dimethylaminocinnamoyl)oxy-2-(1,2-epoxy-1, 5-dimethyl-4-hexenyl)-3-methoxy-1-chloromethyl-1-cyclohexanol The same procedure as Example 5 was repeated but using the compound (100 mg) of Example 14, lithium chloride (41 mg) and acetic acid (0.1 ml), to give 86 mg of the title compound as white solid.

$^1$H-NMR (CDCl$_3$) δ: 7.60 (d, 1H, J=15.8 Hz) 7.41 (d, 2H, J=8.9 Hz) 6.67 (d, 2H, J=8.9 Hz) 6.27 (d, 1H, J=15.8 Hz) 5.71 (m, 1H) 5.22 (brt, 1H) 3.93 (d, 1H, J=11.8 Hz) 3.70 (dd, 1H, J=2.8, 11.0 Hz) 3.52 (d, 1H, J=11.8 Hz) 3.45 (s, 3H) 3.02 (s, 6H) 2.41~1.81 (m, 6H) 1.75 (s, 3H) 1.67 (s, 3H) 1.22 (s, 3H) 1.15~1.06 (m, 1H)

Pharmaceutical Preparation Example
1. Preparation of Tablet

| Active ingredient | 5.0 mg |
|---|---|
| Lactose BP | 150.0 mg |
| Starch BP | 30.0 mg |
| Pregelatinized corn starch BP | 15.0 mg |
| Magnesium stearate | 1.0 mg |

Active ingredient was sieved, mixed with lactose, starch and pregelatinized corn starch. To the mixture, purified water was added. The paste was granulated, dried, mixed with magnesium stearate, and then compressed to obtain tablet.

2. Preparation of Capsule

| Active ingredient | 5.0 mg |
|---|---|
| Starch 1500 | 100.0 mg |
| Magnesium stearate BP | 1.0 mg |

Active ingredient was sieved, and mixed with additives. This mixture was filled in gelatin capsule to give the capsule.

3. Preparation of Injection

| Acitive ingredient | 100 g/ml |
|---|---|
| d-HCl | to be pH 3.5 |
| Saline for Injection BP | maximum 1 ml |

Active ingredient was dissolved in proper volume of saline for injection BP. The pH of the resultant solution was controlled with d-HCl BP to be pH 3.5, and then its volume was controlled with saline for Injection BP. The solution mixed completely was filled in 5-ml type 1 ample maken of glass. The top of ample was fused for sealing. The solution contained in ample was autoclaved at 120° C. for 15 min to be sterilized and to obtain an injection.

Examination of the Inhibiting Activity on Angiogenesis (In Vitro)

The compound sample dissolved in DMSO was diluted to ten times by using MEM culture medium (in case of CPAE cells) without adding FBS (Fetal Bovine Serum), and RPMI 1640 culture (in case of EL-4 and P388D1 cells), and 20 μl of the solution was poured to each well of 96 well plate in triplicate for every concentration gradient. Then, each cell suspension was prepared and poured to examine the inhibiting activity on angiogenesis.

In case of CPAE (Calf Pulmonary Artery Endothelial) cells (used after 2–3 subcultures), a cell suspension having $7 \times 10^3$ cells/ml was prepared with MEM (+10% FBS+50 μg/ml ECGS) medium, and after pouring the suspension (180 μl) to each well of 96 well plate, they were cultured in a $CO_2$ incubator (5% $CO_2$, humidified) for 4 days. The inhibiting activity on angiogenesis was measured by means of SRB method, and the results are shown in Table 1.

In case of EL-4 (Lymphoma, murine) and P388D1 (leukemia, mouse) cells, a cell suspension having $1 \times 10^4$ cells/ml was prepared with RPMI1640 (+10% FBS) culture medium, and after pouring the suspension (180 μl) to each well of 96 well plate, they were cultured in a $CO_2$ incubator (5% $CO_2$, humidified) for 3 days. The inhibiting activity on angiogenesis was measured by means of MTT method, and the results are shown in Table 1.

TABLE 1

The result of IC50 (g/ml)

| | Cell lines | | |
|---|---|---|---|
| The compound | CPAE | EL-4 | P388 |
| Fumagillin | $3.2 \times 10^{-3}$ | $1.6 \times 10^{-3}$ | $\geq 10$ |
| Compound of Example 2 | $1.7 \times 10^{-6}$ | $2.2 \times 10^{-6}$ | $\geq 10$ |
| Compound of Example 3 | $8.9 \times 10^{-8}$ | $1.1 \times 10^{-8}$ | $\geq 10$ |
| Compound of Example 4 | $9.9 \times 10^{-4}$ | $8.4 \times 10^{-4}$ | $\geq 10$ |
| Compound of Example 5 | $4.8 \times 10^{-8}$ | $1.1 \times 10^{-8}$ | $\geq 10$ |
| Compound of Example 7 | $1.2 \times 10^{-5}$ | $5.4 \times 10^{-5}$ | $\geq 10$ |
| Compound of Example 9 | $4.4 \times 10^{-6}$ | $6.6 \times 10^{-6}$ | $\geq 10$ |
| Compound of Example 11 | $2.1 \times 10^{-7}$ | $3.2 \times 10^{-7}$ | $\geq 10$ |
| Compound of Example 12 | $7.3 \times 10^{-7}$ | $6.9 \times 10^{-7}$ | $\geq 10$ |

TABLE 1-continued

The result of IC50 (g/ml)

| The compound | Cell lines | | |
|---|---|---|---|
| | CPAE | EL-4 | P388 |
| Compound of Example 13 | $1.1 \times 10^{-6}$ | $1.6 \times 10^{-6}$ | $\geq 10$ |
| Compound of Example 14 | $6.3 \times 10^{-7}$ | $4.9 \times 10^{-7}$ | $\geq 10$ |
| Compound of Example 15 | $2.5 \times 10^{-6}$ | $4.3 \times 10^{-6}$ | $\geq 10$ |
| Compound of Example 17 | $1.2 \times 10^{-6}$ | $1.5 \times 10^{-6}$ | $\geq 10$ |
| Compound of Example 18 | $5.2 \times 10^{-7}$ | $4.1 \times 10^{-7}$ | $\geq 10$ |
| Compound of Example 19 | $3.2 \times 10^{-7}$ | $5.7 \times 10^{-7}$ | $\geq 10$ |
| Compound of Example 20 | $1.2 \times 10^{-7}$ | $2.2 \times 10^{-7}$ | $\geq 10$ |
| Compound of Example 21 | $8.3 \times 10^{-7}$ | $8.2 \times 10^{-7}$ | $\geq 10$ |
| Compound of Example 25 | $3.3 \times 10^{-7}$ | $4.1 \times 10^{-7}$ | $\geq 10$ |

As can be seen from the results of Table 1, the compounds according to the present invention and salts thereof strongly restrains proliferation of endodermal cells of blood vessels to inhibit angiogenesis.

INDUSTRIAL APPLICABILITY

Thus, the compounds of Chemical Formula 1 according to the present invention and salts thereof can be used as an angiogenesis inhibitor.

We claim:

1. A compound, or a pharmaceutically acceptable salt thereof, represented by Formula 1:

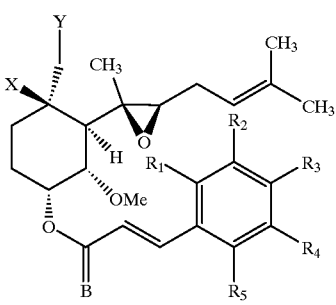

wherein:
   a) X is —OH and Y is halogen or
      X and Y taken together form an oxirane ring;
   b) B is selected from O and $H_2$; and
   c) $R_1, R_2, R_3, R_4$ and $R_5$ are independently chosen from —H, —OH, acetoxy, substituted or unsubstituted amino, substituted or unsubstituted alkyl, substituted or unsubstituted aminoalkoxy, $C_1$–$C_6$ alkoxy, halogen, cyano, trifluoromethyl, nitro, alkylenedioxy, formyl, acetamido and methylenoxycarboxy, with the proviso that $R_1, R_2, R_3, R_4$ and $R_5$ are not each —H.

2. A compound, or a pharmaceutically acceptable salt thereof, according to claim 1, wherein $R_1, R_2, R_3, R_4$ and $R_5$ are independently chosen from —H, —OH, acetoxy, amino, alkylamino, dialkylamino, dialkylaminoalkyl, akylaminoalkoxy, dialkylaminoalkoxy, $C_1$–$C_6$ alkoxy, halogen, cyano, trifluoromethyl, nitro, and methylenedioxy.

3. A compound according to claim 1, chosen from the group consisting of:

O-(3,4-dimethoxycinnamoyl)fumagillol,
O-(4-methoxycinnamoyl)fumagillol,
O-(3,4,5-trimethoxycinnamoyl)fumagillol,
O-(4-Chlorocinnamoyl)fumagillol,
4-(3,4,5-trimethoxycinnamoyl)oxy-2-(1,2-epoxy-1,5-dimethyl-4-hexenyl)-3-methoxy-1-chloromethyl-1-cyclohexanol,
O-(4-trifluoromethylcinnamoyl)fumagillol,
O-(4-nitrocinnamoyl)fumagillol,
O-(3,4-dimethoxy-6-nitrocinnamoyl)fumagillol,
O-(4-acetoxycinnamoyl)fumagillol,
O-(4-hydroxycinnamoyl)fumagillol,
O-(4-acetoxy-3,5-dimethoxycinnamoyl)fumagillol,
O-(3,5-dimethoxy-4-hydroxycinnamoyl)fumagillol,
4-(4-methoxycinnamoyl)oxy-2-(1,2-epoxy-1,5-dimethyl-4-hexenyl)-3-methoxy-1-chloromethyl-1-cyclohexanol,
O-(4-dimethylaminocinnamoyl)fumagillol,
O-(4-aminocinnamoyl)fumagillol,
O-(4-cyanocinnamoyl)fumagillol,
O-(3,4,5-trimethoxycinnamyl)fumagillol,
O-(4-dimethylaminoethoxycinnamoyl)fumagillol,
O-(3-dimethylaminomethyl-4-methoxycinnamoyl) fumagillol,
O-(3,4-methylenedioxycinnamoyl)fumagillol,
O-(3,4-dimethoxy-6-aminocinnamoyl)fumagillol,
O-(4-ethylaminocinnamoyl)fumagillol,
O-(4-ethylaminoethoxycinnamoyl)fumagillol,
O-(4-dimethylaminocinnamyl)fumagillol, and
4-(4-dimethylaminocinnamoyl)oxy-2-(1,2-epoxy-1,5-dimethyl-4-hexenyl)-3-methoxy-1-chloromethyl-1-cyclohexanol.

4. A compound according to claim 1, wherein the pharmaceutically acceptable salt thereof is selected from the hydrochloride, bromate, sulfate, phosphate, nitrate, formate, acetate, trifluoroacetate, oxalate, fumarate, tartarate, maleate, methanesulfonate, benzenesulfonate and p-toluenesulfanate salt.

5. A process for preparing a compound, or a salt thereof, of Formula 5, said process comprising the steps of:
   a) reacting a fumagillol compound with a compound of Formula 3

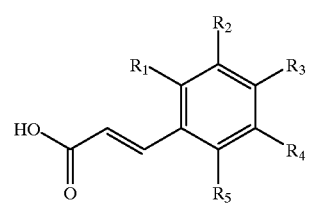

or a corresponding acid-anhydride, mixed anhydride, acid chloride, acid p-toluenesulfonic anhydride, acid mesylic anhydride, 2-pyridine thiol ester or phenyl ester; and b) obtaining a compound of Formula 5,

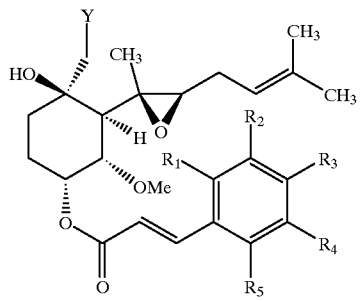

5 wherein

Y is halogen; and $R_1$, $R_2$, $R_3$, $R_4$ and $R_5$ are independently chosen from —H, —OH, acetoxy, substituted or unsubstituted amino, substituted or unsubstituted alkyl, substituted or unsubstituted aminoalkoxy, $C_1$–$C_6$ alkoxy, halogen, cyano, trifluoromethyl, nitro, alkylenedioxy, formyl, acetamido and methylenoxycarboxy, with the proviso that $R_1$, $R_2$, $R_3$, $R_4$ and $R_5$ are not each —H.

6. A process for preparing a compound, or a salt thereof, of Formula 8, said process comprising the steps of:

a) reacting a fumagillol compound with a compound of Formula 6

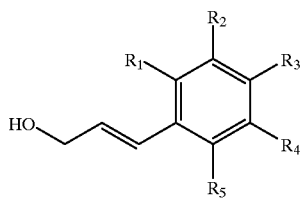

6 or the corresponding tosylate, mesylate or halide; and b) obtaining a compound of Formula 8,

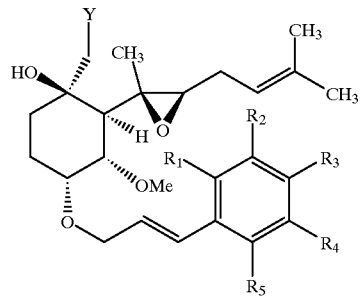

8 wherein

Y is halogen; and $R_1$, $R_2$, $R_3$, $R_4$ and $R_5$ are independently chosen from —H, —OH, acetoxy, substituted or unsubstituted amino, substituted or unsubstituted alkyl, substituted or unsubstituted aminoalkoxy, $C_1$–$C_6$ alkoxy, halogen, cyano, trifluoromethyl, nitro, alkylenedioxy, formyl, acetamido and methylenoxycarboxy, with the proviso that $R_1$, $R_2$, $R_3$, $R_4$ and $R_5$ are not each —H.

7. A pharmaceutical composition for inhibiting angiogenesis in a mammal, said composition comprising a therapeutically effective amount of a compound, or a pharmaceutically acceptable salt thereof, according to claim 1, and a pharmaceutically acceptable carrier.

\* \* \* \* \*